(12) United States Patent
Hansen (10) Patent No.: US 8,991,408 B2
(45) Date of Patent: Mar. 31, 2015

(54) DEVICE FOR CLEANING INSTRUMENT CHANNELS

(75) Inventor: Norbert Hansen, Emmingen (DE)

(73) Assignee: Karl Storz GmbH & Co. KG (DE)

( * ) Notice: Subject to any disclaimer, the term of this patent is extended or adjusted under 35 U.S.C. 154(b) by 1310 days.

(21) Appl. No.: 12/643,776

(22) Filed: Dec. 21, 2009

(65) Prior Publication Data
US 2010/0163074 A1    Jul. 1, 2010

(30) Foreign Application Priority Data

Dec. 22, 2008  (DE) .......................... 10 2008 064 205
Mar. 4, 2009   (DE) .......................... 10 2009 011 204

(51) Int. Cl.
*B08B 9/04*    (2006.01)
*B08B 9/043*   (2006.01)
*A61B 19/00*   (2006.01)

(52) U.S. Cl.
CPC ............... *B08B 9/0436* (2013.01); *A61B 19/34* (2013.01); *A61B 2019/343* (2013.01)
USPC ................ 134/104.2; 134/166 R; 134/166 C; 15/104.05; 15/104.066

(58) Field of Classification Search
None
See application file for complete search history.

(56) References Cited

U.S. PATENT DOCUMENTS

| | | | | |
|---|---|---|---|---|
| 3,205,518 | A * | 9/1965 | Romaine | 15/104.165 |
| 5,964,004 | A | 10/1999 | Bean | |
| 2006/0162105 | A1 * | 7/2006 | Abe | 15/104.2 |
| 2008/0156666 | A1 * | 7/2008 | Panek | 206/1.5 |

FOREIGN PATENT DOCUMENTS

| | | |
|---|---|---|
| DE | 20012968 U1 | 2/2001 |
| DE | 102006001076 A1 | 7/2006 |
| DE | 102006022366 B3 | 1/2008 |
| DE | 202007000793 U1 | 5/2008 |
| DE | 69937496 T2 | 10/2008 |
| EP | 1348352 A2 | 10/2003 |
| EP | 1839565 A2 | 10/2007 |
| EP | 1105061 B1 | 11/2007 |

(Continued)

OTHER PUBLICATIONS

Computer Translation of JP2008-284317 by Nishimura, published Nov. 27, 2008.*
Computer Translation of JP2006-051057 by Sato, published Feb. 23, 2006.*
European Office Action; Application No. EP 09 015 711.6-2307; Feb. 3, 2011; 4 pages.

(Continued)

*Primary Examiner* — Michael Kornakov
*Assistant Examiner* — Ryan Coleman
(74) *Attorney, Agent, or Firm* — St. Onge Steward Johnston & Reens LLC (57) ABSTRACT

A device for cleaning channels including a rod-shaped carrier element, at least one cleaning element that is connected with the carrier element, and at least one additional cleaning element that can be detached from the carrier element. A method for cleaning instrument channels wherein the cleaning device is moved in the axial direction in the instrument channel as far as an end point; after reaching the end point the cleaning device is moved back in the opposite axial direction in the instrument channel. Owing to the reverse motion of the cleaning device, the detachable cleaning element is released from the carrier element and thereafter is no longer part of the cleaning process of the previously cleaned instrument channel and can no longer soil the channel. The device and method removes from the instrument channel the substances that are to be removed and produces an efficient and good cleaning result.

13 Claims, 3 Drawing Sheets

(56) References Cited

FOREIGN PATENT DOCUMENTS

| JP | 2006-051057 | * | 2/2006 |
| JP | 2008-284317 | * | 11/2008 |
| WO | 2006123941 A1 | | 11/2006 |

OTHER PUBLICATIONS

European Search Report; Application No. EP 09 01 5711; May 27, 2010; 4 pages.

* cited by examiner

DEVICE FOR CLEANING INSTRUMENT CHANNELS

CROSS-REFERENCE TO RELATED APPLICATIONS

The present application claims priority of German patent applications Nos. 10 2008 064 205.3 filed on Dec. 22, 2008 and 10 2009 011 204.9 filed on Mar. 4, 2009. All prior applications are herein incorporated by reference in their entirety.

FIELD OF THE INVENTION

The present invention relates to a method and a device for cleaning soiled instrument channels, in particular for the efficient cleaning of channels in medical instruments.

BACKGROUND OF THE INVENTION

If a reusable medical instrument is being used with a patient, then it requires cleaning after its application to the patient. Cleaning of instrumental channels of medical products is particularly difficult.

German patent application DE 2006 001 076 A1 discloses a cleaning brush composed of a long, flexible carrier element and a digitally attached brush head. A section of the carrier element extends beyond the bridge head on its digital side. Lengthening the rod-shaped carrier element avoids the scattering of liquids by a swinging or springing motion by the carrier element. Thanks to the distribution of impure materials in the instrument channel by the brush, cleaning with this cleaning brush does not yield a satisfactory cleaning result.

European patent application EP 1105061 B1 discloses a method and device for cleaning a soiled lumen of an endoscope, by which the impure materials are distributed uniformly inside the instrument channel by pulling and pushing the cleaning device in the instrument channel. Thereafter, this film uniformly distributed in the channel is treated with an enzymatic cleaning liquid. In this case the cleaning device does not serve to remove substances that are to be expelled from the instrument channel, but rather serves for uniform distribution to improve the subsequent treatment with an enzymatic cleaning liquid. The cleaning effect is not sufficient.

The design patent DE 20200700793 U1 discloses a cleaning wick for an instrument channel of a medical instrument. It shows a wick that comprises an adhesive flocking in a partial area. The fibers consist of synthetic material or else natural fibers. When using this cleaning device, the total soiling is distributed after a single pass through the instrument channel, upon withdrawing the cleaning device in the instrument channel. It is necessary to perform a subsequent treatment with cleaning fluid or a repeated cleaning after washing the fibers of the cleaning device.

It is the object of the invention to disclose a method and a device for cleaning medical instrument channels that produce an efficient, good cleaning result.

SUMMARY OF THE INVENTION

The present invention fulfills this object by means of the cleaning device with a rod-shaped carrier element and at least one cleaning element connected with the carrier element, where the cleaning element can be detached from the carrier element, and/or a cleaning method including the steps of moving the cleaning device in the axial direction in the instrument channel up to an end point, so that after reaching the end point the cleaning device is moved outward in the opposite axial direction in the instrument channel and a detachable cleaning element is separated from the carrier element and then is no longer part of the cleaning process of the previously cleaned instrument channel. Advantageous adaptations of the invention are given in the subsidiary claims.

The cleaning device in accordance with the present invention contains a rod-shaped carrier element with cleaning elements. The cleaning elements show at least one fixed cleaning element and in addition at least one detachable cleaning element that can be slid axially on the carrier element. As a result of this multi-partite structure of the cleaning elements on the rod-shaped carrier element, any distribution of impurities in the instrument channel can be reduced as much as possible. The multiform structure of the cleaning element serves the purpose of releasing a detachable element positioned on a fixed cleaning element—said detachable element picking up or combining the majority of impurities by pushing the cleaning device forward through the instrument channel—after the typically one-time motion in the axial direction of the instrument channel up to an end point.

In the subsequent withdrawal of the cleaning device through the instrument channel, this detachable cleaning element is released from the carrier element and is no longer part of the ensuing typical cleaning process. In this manner, any distribution of impurities in the instrument channel, especially those adhering to the detachable cleaning element, is reduced, because a major portion of the impurities are separated from the cleaning device by the detachable cleaning element. Cleaning with the present cleaning device is therefore more efficient and reduces the impurities in the already cleaned instrument channel.

Through the releasing of the detachable cleaning element from the carrier element, there is the additional advantage that on removing the cleaning device from the instrument channel, the extending carrier element on which the distally positioned detachable cleaning element is inserted, prevents any uncontrolled spraying of cleaning fluids and the like that may have been used, by its protrusion, during removal of the remaining cleaning device from the instrument channel. In this manner it is possible to reduce any spraying contamination of the surroundings with possibly infectious material.

The terms "detachable" and "fixed," as used in the foregoing and hereafter, indicate various detaching and fixing possibilities between the cleaning element and the carrier element. In this respect, the term "detachable" is understood to mean a type of connection that allows a sliding of the cleaning element on the carrier element and thus a separation from the carrier element, for instance by slipping or pushing down the cleaning element from the carrier element. Alternatively, the cleaning element, with a part of the carrier element, can also be separated from the rest of the carrier element at a foreseen cut-off point, for instance by means of breaking at a predetermined fracture point or by severing it at a defined cut-off point. The term "fixed" designates a connection that does not allow any sliding of the cleaning element on the carrier element because of the axial motion of the instrument channel. The connection between the cleaning element and the carrier element is preserved during the cleaning process.

In a particular embodiment, at least one cleaning element is connected with the carrier element and is configured so that it can be separated from the carrier element.

A renewed distribution of the impurities, in particular, that are connected to the detachable cleaning element is reduced in the instrument channel because a great portion of the impurities was separated from the cleaning device through the separation of the cleaning element from the cleaning device.

A cleaning is extremely efficient and reduces the impurities in the already cleaned instrument channel. This configuration offers the additional advantage that the cleaning device itself shows a high cleaning quality because of the separation of the cleaning element from the carrier element.

One embodiment of the present invention shows that at least one detachable cleaning element is positioned distally on the carrier element and at least one fixed cleaning element is positioned proximally to said first element.

This has the advantage that upon withdrawing the cleaning device, the detachable cleaning element can detach itself from the carrier element and in this manner the impurities already collected on the detachable cleaning element are not distributed in the already cleaned instrument channel. The cleaning of the instrument channel is therefore more efficient and allows a better cleaning result.

Preferably, the detachable cleaning element is attached to the carrier element by a lubricious connection. It is possible not to push the detachable cleaning element onto the carrier element, but rather to slide it through the instrument channel with the carrier element and the fixed cleaning element. Preferably, however, it is advisable to equip the detachable cleaning element with a bored aperture, through which the carrier element can be pinned onto the detachable cleaning element in sliding fashion. This allows the detachable cleaning element to be slid uniformly through the channel and prevents any irregular deforming of the cleaning element.

It has been demonstrated, in particular, that part of the carrier element can be detached with at least one cleaning element by means of a cut-off point provided on the distal end of the carrier element.

This embodiment has the advantage that the soiled cleaning element, after it emerges from the instrument channel, can be detached by the carrier element independently of its shape, its material, and its stretch properties, and in this way the impurities already collected and no longer distributed in the instrument channel. The cleaning of the instrument channels is therefore far more efficient.

In a particular embodiment, several fixed cleaning elements are secured on the rod-shaped carrier element such as to allow an intermediate space with respect to one another. These inventive intermediate spaces have the advantage that within these spaces it is also possible to transport larger collections of impurities, which can fall away or can be manually removed after one passage of the cleaning device through the instrument channel with the detachable cleaning element. In addition, they allow a spreading of the cleaning elements into the instrument channel in the axial direction, leading to an improved cleaning result. Preferably the carrier element is provided with a stop, which restricts the slidability of the cleaning element on the carrier element.

The stop provided for limiting the slidability of the cleaning element prevents the cleaning element from detaching itself from the carrier element during the cleaning process and remaining stuck in the instrument channel. This manner of fixing a cleaning element on the carrier element has the additional advantage that the user can assemble his cleaning device in modular fashion, for instance by making possible the limiting of the slidability of the cleaning elements with synthetic elements, which he can apply distally from the proximal and/or distal end of the cleaning element.

It has been shown that the area of the carrier element on which the cleaning element is fixed has, because of the addition or removal of material, the property of fulfilling the purpose of a fixing of the cleaning elements. For instance, applying a metallic structure to the area of the carrier element can enlarge the diameter of the carrier element at this spot, so that a cleaning element that includes a borehole with the diameter of the rest of the carrier element and is pushed onto the rod-shaped carrier element is fixed. An adhesive connection constitutes another preferred possibility for fixing the cleaning element on the carrier element.

In a preferred configuration for fixing a cleaning element on the carrier element, areas for fixing onto the carrier element with a thread are provided and fixed thereto so that the cleaning elements to be fixed can be screwed on. This configuration offers the advantage that the carrier element can be prepared anew after its use and, once provided with new cleaning elements, can be applied again to the cleaning of instrument channels. A carrier element that has been prepared anew can be selected as more worthwhile in its material properties and in its design, because it can be used repeatedly for the cleaning of diverse channels. The combination of the cleaning elements as a disposable article and the carrier element as a reusable article therefore offers a considerably more valuable material configuration and likewise cost reduction. During the cleaning process the material can be put under greater pressure through the use of more valuable materials, leading to a better, more efficient cleaning result.

The cleaning elements are preferably constructed of a material with compressible properties. A material with compressible properties, preferably with felt-type properties, allows compression of the cleaning element upon insertion into the instrument channel. In this manner the cleaning element is compressed upon shoving the cleaning device onto the instrument channel. This allows a higher abrasive property of the cleaning elements. As a result, greater impurities for instance, as well as hardened substances adhering to the instrument channel, can be removed better. By using the compressible material, the spraying of cleaning liquid and collected impurities in the instrument channel upon removal of the cleaning device from the instrument channel can be avoided because the cleaning elements stretch more uniformly upon removal because of the compressible material.

In an especially preferred embodiment, at least one cleaning element can take up and exude a liquid. As a result of the combination of the cleaning device with a liquid, in particular water or a liquid with cleansing properties such as by using enzymatic substances, the cleaning process can be clearly optimized. Preferably not all cleaning elements are provided with a liquid, so that the other cleaning elements on the carrier element can absorb the liquids from the instrument channel. In an additional embodiment the diameter of the cleaning elements is selected so that it is larger than the smallest and largest diameter of the instrument channel that is to be cleaned.

If the cleaning elements were to have a smaller diameter than the smallest and largest diameter of the instrument channel, then upon sliding the cleaning device through the instrument channel in the axial direction, the cleaning elements would not continually touch and clean the channel interior.

A larger diameter of the cleaning elements than the smallest and largest diameter of the instrument channels, which can also vary in its diameter, therefore prevents a back-and-forth motion of the carrier element diagonally to the instrument channel during the cleaning process by specialized personnel, because the material of the cleaning elements all around the entire channel wall is pressed together. In this manner in particular it is possible to prevent damage, especially by the carrier element in the instrument channel, because the cleaning device is moved uniformly through the instrument channel and an efficient cleaning result is achieved.

It has been shown in particular that the outer form of the cross-section of the cleaning elements corresponds to the cross-section of the instrument channel that is to be cleaned.

This has the advantage that by means of the same configuration a uniform compression of the material of the cleaning elements, as well as an easier insertion and sliding of the cleaning device through the instrument channel, can be realized. As a result of this arrangement, a lower use of force needs to be applied in moving the cleaning device back and forth in the instrument channel, which clearly reduces the risk of damage inside the instrument channel by erroneous operation and makes the cleaning process more comfortable for the specialized personnel. In addition, owing to this configuration, depending on the choice of the proportion of the dimensions of the cross-section of the instrument channel and cleaning elements to one another, the abrasive property of the cleaning device can be modulated and the cleaning needs can be taken into account.

In a particular embodiment of the cleaning device, the degree of hardness of the cleaning elements varies along the rod-shaped carrier element.

Owing to this diverse degree of hardness, the cleaning device can be used both for combining and removing larger impurities as well as for absorbing existing liquids that are found increasingly in the instrument channel after the use of a medical instrument on the patient. In this process the cleaning elements with the lower degree of hardness absorb the liquids and impurities present in the instrument channel, while the cleaning elements whose materials show a higher degree of hardness because of their higher abrasive properties, remove and combine together larger and more adherent substances from the instrument channel.

According to a particularly preferred embodiment, the hardness properties of the cleaning elements decrease in the direction from proximal to distal on the carrier element.

In this particular configuration of the arrangement of the cleaning elements with various hardness properties, there is the advantage that the cleaning device, along with the absorption of liquids and the collection of impurities, can be more easily inserted into the instrument channel. The arrangement of the cleaning elements of diverse hardness properties on the carrier element can, however, also be increasing in the reverse direction.

In one embodiment, at least one cleaning element on the carrier element has a hardness gradient of compressible material that varies in the direction from proximal to distal.

This gradient leads to a particularly good cleaning result, even if the carrier element is equipped only with few cleaning elements. Thus, for instance, only with a cleaning element that is very long in the axial direction can the impurities in the instrument channel be efficiently combined together.

Preferably the cleaning elements on the carrier element are of diverse materials.

The design of the cleaning elements on a carrier element with diverse materials allows the adaptation of the cleaning device to the diverse requirements that frequently arise in practice. Thus, for instance, a device can be selected for the cleaning of an irrigation channel that has cleaning elements which consist of an elastic synthetic material whose sides are provided with a blade edge. The combination of cleaning elements with felt-type properties with cleaning elements of synthetic material, for instance a spongy material, is also very effective especially when using cleaning liquids.

In a particular embodiment, the cleaning elements on a carrier element have different diameters. In a special configuration of this model, the diameters of the cleaning elements are positioned in declining order from the proximal to the distal side.

As a result the insertion of the cleaning device into the instrument channel and thus the handling is simplified, but because of the decreasing diameters of the cleaning elements from proximal to distal side, the cleaning elements decreasing from proximal to distal side are compressed to varying degrees, so that because of this configuration the strongly compressed cleaning elements show a stronger combining or abrasive function and the less compressed cleaning elements show instead an increasing function. The arrangement of the diverse diameters of the cleaning elements can also vary, however, or else can be selected as decreasing from the distal to the proximal side. It has proven especially beneficial to optimize the slidability of the distally situated cleaning elements on the carrier element by coating the area of the carrier element that is situated distally to the fixed cleaning element preferably with an especially lubricious surface, for instance with Teflon, or by making it from a corresponding low-friction material.

The rigid rod-shaped carrier element can also be coated with a low-friction synthetic material, such as polytetrafluorethylene (PTFE), or with another lubricious material such as Teflon.

Such a low-friction realization of the surface of the rod-shaped carrier element facilitates the removal of the detachable cleaning element from the carrier element after a single passage through the instrument channel and in addition, upon contact of the carrier element with the instrument channel that is to be cleaned, prevents damage to the channel of the instrument. It has been shown that it is advantageous to choose for the carrier element a rigid material, in particular steel. The term "rigid," as used here, is understood to mean a material that has a high buckling resistance, stability, and cannot be deformed. This makes possible a very reliable and safe cleaning, especially for straight, rigid endoscopes. Depending on the size of the cross-section, the material can also have elastic properties or can be made of an elastic material so that the cleaning device is well adapted to the shape of the instrument channel and also can be used for cleaning flexible and possibly bent medical instruments. An additional possibility is to segment the rod-shaped carrier element to reach various areas with elastic and deformable properties and to be able to clean especially efficient, difficult channel geometries.

In a preferred embodiment, the carrier element is made of a solid material. If the rod-shaped carrier element consists of solid material, then despite small cross-section surfaces, which are often used in cleaning channels of small instruments with small diameters, it can have very high stability and resistance to buckling. In particular, the solid material also offers the advantage that no impurities can collect in the carrier element that, in turn, need to be cleaned with a cleaning device if the carrier element takes the form of a reprocessed product.

It has been shown in particular that the carrier element comprises a phase at its ends.

A phase at the ends of the carrier element has the advantage that damage that can be caused by the cleaning device in the instrument channel, for instance by grazing along the channel surface, can be avoided and in addition that introduction of the cleaning device into the instrument channel is supported.

Preferably a marker is provided on the carrier element constituting a measurement for the insertion depth of the cleaning device in the instrument channel and representing the desired end position of the cleaning device in the instrument channel.

This has the advantage that all parts of the instrument channel are reliably cleaned and the marker enables the user to clean the instrument channel completely without moving the device unnecessarily far outside the channel in the distal direction. Thus the detachable cleaning element, corresponding to the position of the marker, for instance, can be pushed out of the instrument channel only so far that part of the cleaning element remains inside the instrument channel and is fixed in such a way that it can, however, be manually removed from the channel. The detachable cleaning element, in this manner, does not fall uncontrollably out of the instrument channel, and an uncontrolled distribution of collected substances into the environment by the detachable cleaning element is avoided. Alternatively, the position of the marker can also be selected in such a way that the detachable cleaning element extends entirely out of the channel in the distal direction and becomes detached when pulled back. The handling of the cleaning device is therefore further improved by this marker.

It has been shown to be advantageous to provide for the cleaning device a container for inserting contaminated cleaning elements with a closeable opening. Through this opening it is possible for at least one cleaning element of the cleaning device to be brought into container interior space. In addition, according to the invention, the container is provided with a device for detaching at least one cleaning element from a carrier element in the container interior.

The container for inserting contaminated cleaning elements offers the advantage that the cleaning elements, after a single passage through the instrument channel and thus after emerging from the instrument channel, are not required to be detached from the carrier element, but rather can be detached automatically, in particular, from the carrier element by a device in the container interior space and conveyed together with the container toward disposal without any contamination of the environment occurring. Here the container can be produced both as a disposable product with just one cleaning element included and as a reusable product after the insertion of several cleaning elements in a disposal container for collecting several contaminated cleaning elements. As a result of using such a container, the risk of a contamination directly by cleaning personnel from soiled and bacteria-laden cleaning elements is considerably reduced. In addition, according to the invention, it is possible to avoid further contamination of the instrument channel by the withdrawal of the soiled cleaning elements through the instrument channel.

In a particular embodiment, at least one cleaning element is detached from the carrier element of the cleaning device by a device for releasing it in the container at a predetermined cut-off point, which is configured for instance as a preset break point or a tapering of the carrier element.

The device for releasing the cleaning element from the carrier element can comprise various mechanisms for releasing the soiled cleaning elements. In a particular embodiment, at least one cleaning element is released by pinching, together with a part of the carrier element, from the cleaning device. For this particular embodiment, a preset break point can also be provided on the carrier element and can be separated for release by pinching off the cleaning device by the device. Another possibility is to twist or pull off the cleaning element from the carrier element. In this embodiment the carrier element would remain unchanged in its originally geometric form and in its length. All these mechanisms for releasing the soiled cleaning elements from the carrier element in the container interior space have the advantage, however, that the carrier element after it is withdrawn can be provided with new cleaning elements again according to a preparation process and can be used for a new cleaning process and that any recontamination of the instrument channel by impurities and bacteria is considerably reduced.

It has been proven advantageous that the container for inserting contaminated cleaning elements of the cleaning device should comprise a sensor, which determines the position of the cleaning element that is to be released in the container interior space and signals it to the device for detaching and said device automatically releases the designated cleaning element from the carrier element by a release mechanism.

The sensor for detecting the position of the cleaning device in the container interior space has the advantage that the soiled and bacteria-laden cleaning elements are safely and completely released from the carrier element at the cut-off point foreseen for this purpose. This can very securely prevent a soiled cleaning element from being only partly released, or not released at all, from the carrier element and from soiling the carrier element again when it is withdrawn through the instrument channel. In a particular embodiment, the sensor indicates to the user the precise position for releasing the soiled cleaning element from the cleaning device, so that the user inserts the cleaning device sufficiently far into the container interior space for the release process of the cleaning elements from the carrier element. In this manner a secure release of the cleaning elements is guaranteed on the basis of the detected and reported position in the container interior space.

A preferred method for cleaning instrument channels of medical instruments with the cleaning device described above includes the following sequence. After insertion in the instrument channel that is to be cleaned, the cleaning device is moved in axial direction in the instrument channel up to an end point, so that after reaching the end point the cleaning device is moved in the opposite axial direction in the instrument channel. In this context the detachable cleaning element is released from the carrier element and is then no longer part of the cleaning process of the previously cleaned instrument channels.

In this manner, a distribution, in particular of the impurities connected with the releasable cleaning element in the instrument channel, is reduced, because a regularly larger portion of the impurities with the detachable cleaning element is separated from the cleaning device. A cleaning with the present cleaning device is therefore more efficient and reduces the remaining impurities in the instrument channel.

The term "end position" as used so far and hereafter is understood as the reverse point of the motion between the motion of the cleaning device in axial direction and the withdrawal in the opposite axial direction through the instrument channel. The end position of the cleaning device can be selected in such a way that the detachable cleaning element emerges at the end of the instrument channel, and that it is removed manually in an additional working step. Another variant is for the cleaning device, previous to the emergence of the detachable cleaning element from the distal end of the instrument channel, to be withdrawn. In this case the detachable cleaning element after the cleaning process is found in the instrument channel and in an additional step is pushed out of the instrument channel with an additional device. An alternative for this purpose is to use a rod or a carrier element with or without cleaning elements. In a preferred embodiment, the end position of the cleaning device is, however, selected in such a way that the cleaning device is pushed into the instrument channel until the detachable cleaning element emerges completely from the distal end of the instrument channel. Upon emerging from the instrument channel, the cleaning element stretches because of its particularly compressible material properties and falls down upon the withdrawal of the cleaning device from the contact with the instrument channel that is to be cleaned. In this manner the detachable cleaning element is no longer mounted slidably on the carrier element and therefore is no longer part of the cleaning process. The introduction of impurities adhering to the detached cleaning element is thus, according to the invention, prevented.

In a particular embodiment, the cleaning device is pushed forward into the instrument channel until at least one cleaning element emerges completely from the distal end of the instrument channel. After the emergence of the cleaning device from the instrument channel, a part of the carrier element with the soiled cleaning element is separated at a site provided for this purpose. In this manner the cleaning element is no longer part of the cleaning process. The introduction of impurities adhering to the released carrier element with the cleaning element is therefore, according to the invention, prevented.

In a preferred method for cleaning instrument channels, at least one cleaning element that is to be detached when the cleaning device is inserted, after emergence of the cleaning device from the distal end of the instrument channel, in a container for inserting contaminated cleaning elements. In the interior space of the container, through the insertion of the cleaning device, a mechanism is triggered which releases the contaminated and soiled cleaning element from the carrier element and, after removal of the carrier element of the cleaning device from the container, said container is closed in sterile manner.

In summary, the present invention in other words reveals a device and a process for removing impurities from the lumen of medical instruments. It consists of a lengthwise base element and at least one cleaning member that is connected with said base element and is characterized in that at least one cleaning member is separated from the base element during back-and-forth motion of the cleaning device in the lengthwise lumen. The process for cleaning the lumen of medical instruments with the inventive device embraces the following steps:

The apparatus for cleaning the lumen of medical instruments is pushed forward in the longitudinal direction of the lumen as far as a reverse point. After reaching the reverse point, the apparatus for cleaning is moved back in the opposite direction through the lumen of the instrument. Because of the reverse motion of the apparatus to cleaning, the slidable, moveable cleaning member is separated from the base element and is then no longer part of the cleaning process of the previously cleaned instrument lumen and can no longer soil said lumen.

A container receives the contaminated, soiled cleaning members and ensures a secure removal of the soiled cleaning members. The present invention discloses a device and a method for cleaning the lumen of medical instruments that securely transport and dispose of removed substances from the instrument lumen and make possible the requirements for an efficient and good cleaning of the lumen according to the invention.

Additional advantages of the present invention can be seen from the following illustrations of several preferred embodiments. The invention is not restricted to these embodiments.

DETAILED DESCRIPTION OF THE INVENTION

Figure 1:
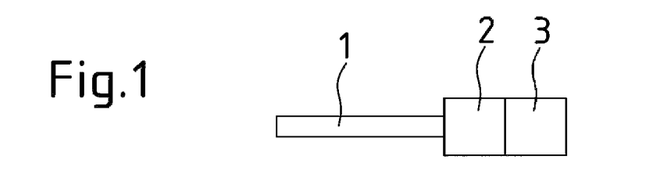
FIG. 1 shows an exemplary inventive cleaning device with a rod-shaped carrier element and with cleaning elements.

The cleaning device illustrated in FIG. 1 shows a carrier element 1 made of a rigid, buckle-resistant, and non-deformable material with cleaning element 2 fixed on the carrier element 1 and with a detachable cleaning element 3 that can slide axially on the carrier element 1.

The carrier element 1 is made of solid material, such as steel, and has a smaller diameter than the instrument channel 4 that is to be cleaned. The carrier element 1 is longer than the instrumental channel 4 that is to be cleaned, so that the cleaning device can still be held sufficiently well with the hand if the cleaning device is pushed completely through the instrument channel 4 in axial direction to the end position. The cleaning device, depending on the length of the instrument channel 4 that is to be cleaned, has a length of 0.5 m to 3 m and a diameter between 0.1 cm and 0.8 cm.

The cleaning elements 2 and 3 have a greater diameter than the smallest diameter of the instrument channel 4 that is to be cleaned. This prevents the need for specialized personnel in cleaning the instrument channel 4 with the inventive cleaning device to make a back-and-forth motion of the carrier element 1 diagonally to the instrument channel 4 for an efficient cleaning. In this manner, in addition, damage to the entry opening, into which the cleaning device is inserted, is prevented in the instrument channel 4, because the cleaning device is uniformly passed through the instrument channel 4.

The cleaning elements 2 and 3 are made of a material with compressible properties, of synthetic material or natural fibers. The structure of the material is felt-like. This has the advantage that cleaning elements 2 and 3 comprise both abrasive and receptive properties. The detachable cleaning element 3 is mounted on the rod-shaped carrier element 1 by a borehole whose diameter is greater than the solid material cross-section of the carrier element 1. Because the area of the carrier element 1 situated distally from the fixed cleaning element 2 has its surface coated with Teflon, the lubricity of the detachable cleaning element 3 on the carrier element 1 is increased, thereby facilitating the detachment from the carrier element according to the invention.

Figure 2:
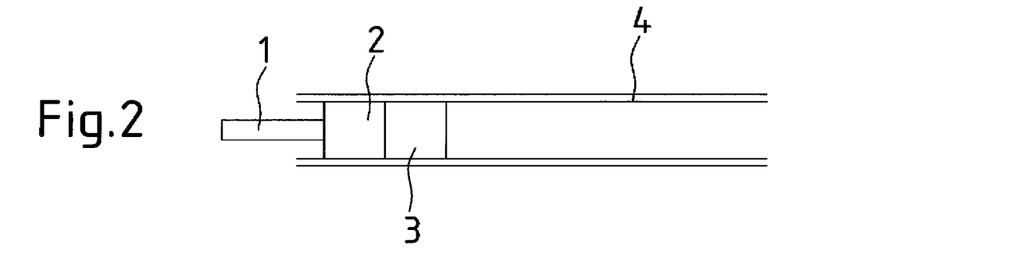
FIG. 2 shows a phase of the inventive cleaning process with the inventive cleaning device at the start of the cleaning process.
Figure 3:
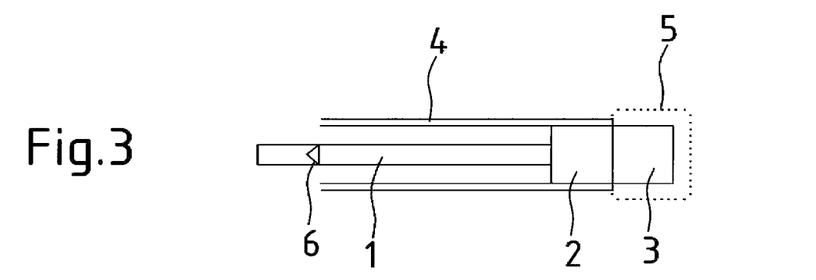
FIG. 3 shows a phase of the inventive cleaning process with the cleaning device in the end position.
Figure 4:
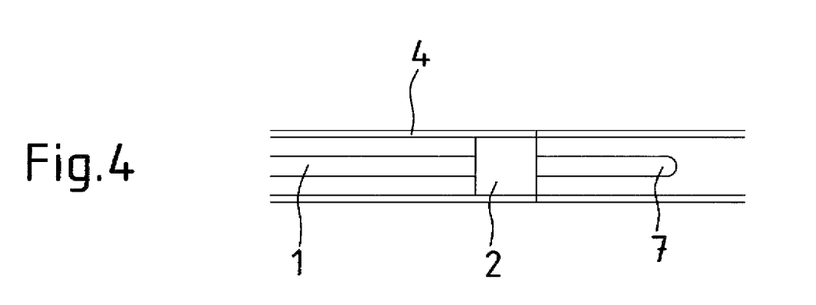
FIG. 4 shows a phase of the inventive cleaning device with the inventive cleaning device after reaching the end point and subsequent withdrawing of the cleaning device.

FIGS. 2, 3, and 4 show the preferred method for cleaning with the inventive cleaning device. The cleaning device with a fixed cleaning element 2 in FIG. 2 comprises on the carrier element an axially slidable, detachable cleaning element 3, which is inserted in an instrument channel 4 that is to be cleaned. The arrangement of one fixed and one detachable cleaning element on a carrier element 1 has the aim that the detachable cleaning element 3, which lies distally to the fixed cleaning element 2, should pick up and assemble more impurities, by the sliding of the cleaning device in the instrument channel 4, than the fixed cleaning element.

FIG. 3 shows the detachment of the cleaning element 2. This occurs at the end point, which is reached here with the complete emergence of the detachable cleaning element 3 from the instrument channel 4. For this purpose the rod-shaped carrier element 1 is equipped with a marker 6, which shows how far the cleaning device is to be inserted by cleaning specialized personnel into the instrument channel 4.

The cleaning device in FIG. 4 shows no detachable cleaning element 3. As a result of pulling back the cleaning device through the instrument channel 4, the detachable cleaning element 3 is released from the carrier element 1 and on emerging from the instrument channel becomes stretched because of its compressible material properties, and is no longer part of the further cleaning process. In this way any distribution, in particular of the impurities connected to the detachable cleaning element 3 in the instrument channel 4, is reduced. The cleaning is therefore very effective.

Figure 5:
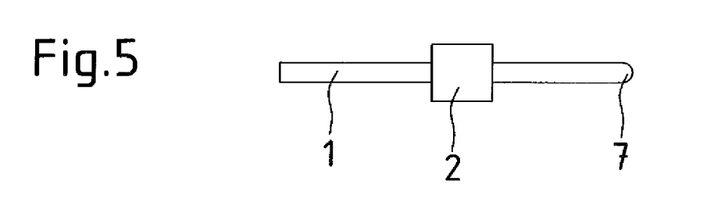
FIG. 5 shows an exemplary inventive cleaning device with a rod-shaped carrier element and with a fixed cleaning element after the inventive cleaning process.

FIG. 5 shows the cleaning device after the cleaning of the instrument channel 4. The detachable cleaning element 3 has detached itself from the carrier element inside the instrument channel because of the reverse motion of the cleaning device. A fixed cleaning element 2 is found on the carrier element. By detaching the cleaning element 3, the result is a protrusion of the carrier element 1 with a section with a phase 7 distally from the fixed cleaning element 2, which reduces any spraying of cleaning liquid and the like after removal of the cleaning device from the instrument channel 4.

Figure 6:
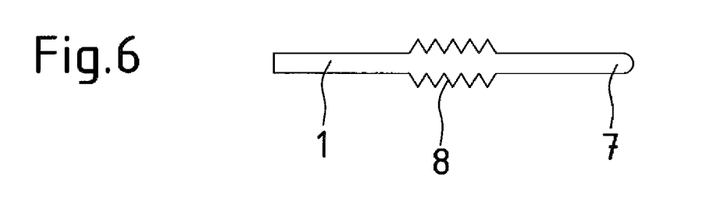
FIG. 6 shows an exemplary realization of a rod-shaped carrier element for an inventive cleaning device.

A particular embodiment of the attachment feature of a fixed cleaning element 2 is shown in FIG. 6. The carrier element 1 shows an area that is equipped with a thread 8. The cleaning element 2 made of felt, which is to be fixed, is screwed onto the thread 8. For this purpose the cleaning element 2 comprises a borehole whose diameter is slightly larger than the nominal diameter of the carrier element 1. This makes possible a defined release of the fixed cleaning element 2 from the carrier element 1.

This offers the advantage that the carrier element 1 can be prepared again by sterilization, for instance, after its use and, equipped with new cleaning elements 2 and 3 that are to be used once, can be applied once more to the cleaning of instrument channels 4. The re-preparation and reuse of the carrier element 1 allow costs to be clearly reduced. The distal end of the carrier element 1 is rounded in order to avoid damage to the instrument channel 4 and to facilitate simpler insertion of the cleaning device in the instrument channel 4.

Figure 7:
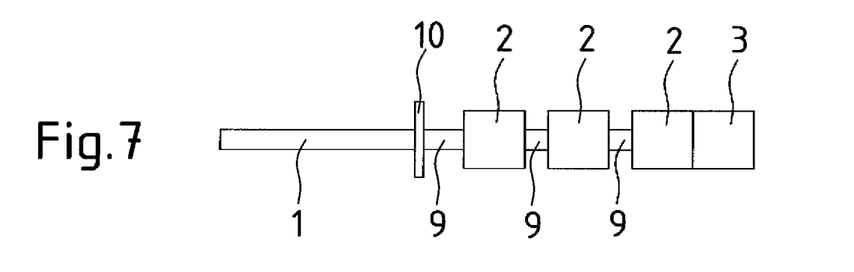
FIG. 7 shows an additional variant of the inventive cleaning device with cleaning elements fixed at distances from one another.
Figure 8:
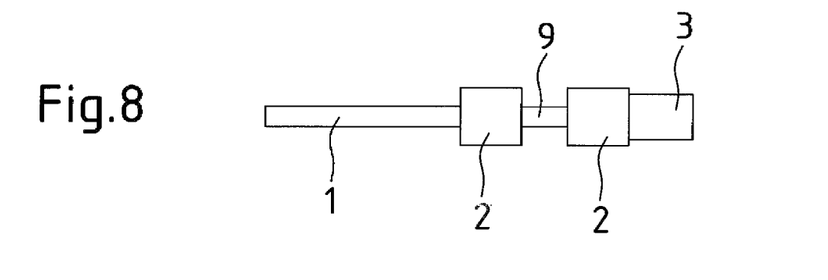
FIG. 8 shows a variant of the inventive cleaning device with several cleaning elements of diverse diameter fixed on the carrier element.

Another particular arrangement of the fixed cleaning elements 2 on the rod-shaped carrier element 1 in accordance with the invention is shown in FIG. 7. There is an intermediate space between the two fixed cleaning elements 2. Thanks to this, impurities that are to be expelled are collected in said space and after passing through the instrument channel 4, on the emergence of the cleaning device out of the instrument channel 4, they can fall away or be manually removed. In this way the impurities collected in the intermediate space 9 are prevented from being redistributed in the instrument channel 4 upon withdrawal of the cleaning device through said channel. These intermediate spaces 9 also facilitate the insertion of the cleaning device, because the cleaning elements 2 and 3 are made of a compressible material and comprise a greater diameter than the instrument channel 4. The intermediate space 9 therefore, according to the invention, offers room in which the cleaning elements 2 and 3 spread out because of their shape change upon entering the instrument channel 4 and in this manner they can adapt well to the channel shape. Several cleaning elements 2, made of felt, are fixed on the carrier element 1. Therefore they have both abrasive and absorbent properties. The proximally situated fixed cleaning element 10 is made of an elastic synthetic material and in addition is equipped with a blade edge 10. This has the advantage that liquids that are not completely registered or picked up by the cleaning elements 2 and 3 are skimmed out of the instrument channel 4.

In the illustrations already described, the diameters of the cleaning elements 2 and 3 on a carrier element 1 are of equal size. FIG. 7 shows an alternative exemplary embodiment of the cleaning device. The cleaning device in FIG. 7 shows several cleaning elements 2 and a detachable cleaning element 3 with various diameters. The diameters are in decreasing size going in the distal direction. This makes possible, first, a simpler insertion of the cleaning device in the instrument channel 4 and, second, because of the varying compression of the cleaning elements 2 and 3 there are diverse degrees of hardness of the cleaning elements 2 and 3, which support the removal, assembling, and absorbing functions of the cleaning device, leading to an especially effective cleaning.

Figure 9:
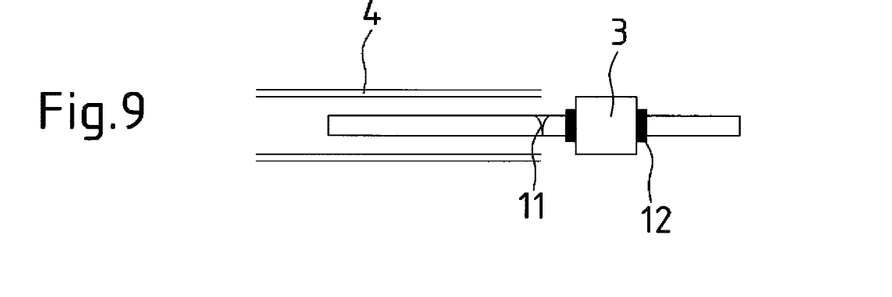
FIG. 9 shows a variant of the inventive cleaning device with a particular fixing possibility of the cleaning element.

An alternative configuration for fixing the cleaning element 3 onto the carrier element and for releasing after emergence from the instrument channel 4 is shown in FIG. 9. The cleaning element 3 is restricted in its slidability on the carrier element 1 by a stop 12 situated proximally and distally on the carrier element 1. These stops 12 in this embodiment are made of synthetic materials, which are mounted firmly against slipping proximally and distally from the cleaning element 3. The cleaning element 3 after its distal emergence from the instrument channel 4 is separated by a cutting device at the predetermined cut-off point 11.

This modular structure of the cleaning device offers the user various possibilities for assembling for individual use in cleaning medical instrument channels.

Figure 10:
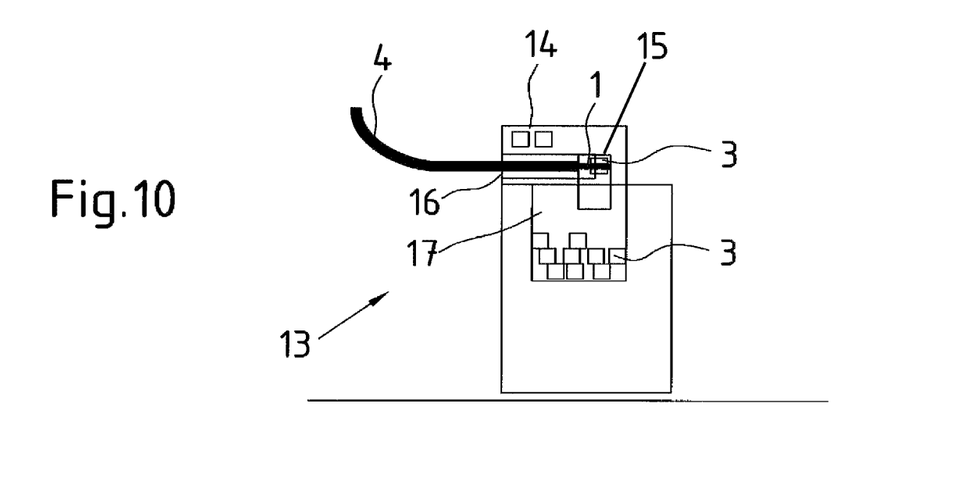
FIG. 10 shows a variant of the inventive cleaning device with a container for inserting and removing contaminated cleaning elements.

FIG. 10 shows an inventive cleaning device. The carrier element 1 with cleaning elements 3, which has passed the distal end of the instrument channel 4, is inserted into the container interior space of the container 13 for receiving contaminated cleaning elements 3.

The container 13 is made of polyethylene, in particular, which guarantees a high degree of rigidity of the container. The cleaning device is inserted with the instrument channel 4 of the endoscopic system into the opening 16 of the container. The opening 16 of the container is equipped with a flap, which can be flipped open by the insertion of the cleaning device. If no removal of cleaning elements takes place, the flap on the opening 16 ensures that the container 13 is closed to bacteria and any contamination of the cleaning personnel is avoided. In the container interior space there is a removable refuse container 17, provided in order to make possible the collection of cleaning elements 3 of several cleaning devices after the detachment from the carrier element 1.

A sensor 14 in the container 13 informs the user of the correct position of the cleaning device in the device for release 15 by means of the sensor signal, so that the separation is performed by pinching off the carrier element 1 in the device 15, which leads to the break-up of the foreseen cut-off point 11 and the cleaning element 3 is released from the carrier element 1 and falls into the refuse container 17 of the container for receiving contaminated cleaning elements 13. As a result, cleaning elements 3 of various cleaning devices can be removed together with the refuse container 17.

Figure 11:
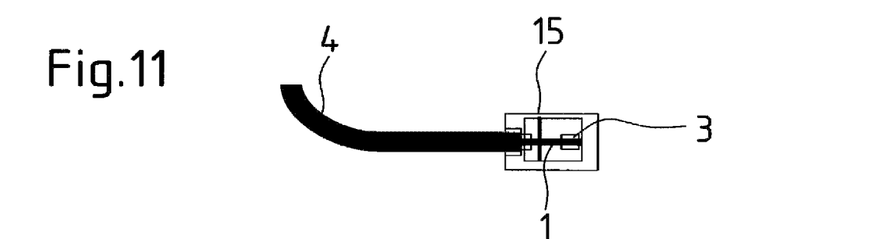
FIG. 11 shows in exemplary fashion an inventive cleaning device with a cleaning element fixed on the carrier element in a device for releasing a cleaning element.

FIG. 11 shows another variant for removing contaminated cleaning elements 3. The device for detaching 15 here is manually inserted by means of a contaminated cleaning element 3, which on the distal side extends out of the endoscopic system. By pressing together the device for release 15, the cleaning element 3 is gripped and exchanged upon drawing back the carrier element 1. After the ensuing removal of the endoscopic system from the device 15, the device 15 closes bacteria-free. The device for release 15 together with the collected contaminated cleaning elements 3 is removed as one unit. After release of the contaminated cleaning elements 3 and removal from the instrument channel, the carrier element 1 is prepared again and can be reused.

What is claimed is:

1. A cleaning device for cleaning channels of medical instruments, the cleaning device comprising:
   a rod-shaped carrier element;
   at least one cleaning element connected with the carrier element by a sliding connection, where the at least one cleaning element is detachable from the carrier element and the sliding connection provides the at least one detachable cleaning element to slide along a longitudinal axis of the carrier element, the at least one detachable cleaning element being detachable from the carrier element in response to withdrawing the cleaning device from a channel of a medical instrument that is cleaned with the cleaning device; and
   at least one cleaning element fixed onto the carrier element, where the at least one fixed cleaning element is immovable along the longitudinal axis of the carrier element.

2. The cleaning device according to claim 1, wherein the at least one detachable cleaning element is positioned distally on the carrier element and the at least one fixed cleaning element is positioned proximally to said detachable cleaning element.

3. The cleaning device according to claim 1, wherein the detachable cleaning element is mounted distally on the carrier element by the sliding connection.

4. The cleaning device according to claim 1, wherein at least one of the detachable cleaning element or fixed cleaning element is constructed of a compressible material.

5. The cleaning device according to claim 1, wherein at least one of the detachable cleaning element or fixed cleaning element is constructed of a material adapted to absorb and emit a cleaning liquid.

6. The cleaning device according to claim 1, wherein the degree of hardness of at least one of the detachable cleaning element or fixed cleaning element varies along the carrier element.

7. The cleaning device according to claim 1, wherein at least one of the detachable cleaning element or fixed cleaning element is constructed of an elastic synthetic material.

8. The cleaning device according to claim 1, wherein the carrier element comprises a rounded surface on at least one end.

9. The cleaning device according to claim 1, wherein the carrier element is rigid and is coated with a synthetic material which minimizes friction.

10. The cleaning device according to claim 1, further comprising a container for receiving contaminated cleaning elements, the container having a closeable opening which provides access for the cleaning device to an interior space of the container, the container having a pinching device, wherein the pinching device separates the at least one detachable cleaning element from the carrier element in the interior space.

11. The cleaning device according to claim 4, wherein the compressible material is felt.

12. The cleaning device according to claim 7, wherein at least one of the detachable cleaning element or fixed cleaning element is provided with a blade edge.

13. The cleaning device according to claim 9, wherein the synthetic material is polytetrafluorethylene.

* * * * *